US00PP30035P3

(12) United States Plant Patent
Lee

(10) Patent No.: US PP30,035 P3
(45) Date of Patent: Dec. 25, 2018

(54) ***ZAMIOCULCAS* PLANT NAMED 'DOWON'**

(50) Latin Name: *Zamioculcas zamiifolia*
Varietal Denomination: Dowon

(71) Applicant: Hyuk Jin Lee, Yongin (KR)

(72) Inventor: Hyuk Jin Lee, Yongin (KR)

( * ) Notice: Subject to any disclaimer, the term of this patent is extended or adjusted under 35 U.S.C. 154(b) by 195 days.

(21) Appl. No.: 15/330,414

(22) Filed: Sep. 16, 2016

(65) Prior Publication Data

US 2018/0084697 P1 Mar. 22, 2018

(51) Int. Cl.
*A01H 5/02* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373, 379
CPC ..... A01H 5/12
See application file for complete search history.

(56) References Cited

PUBLICATIONS

UPOVROM Plant Variety Database citation for 'Dowon' as per QZ PBR 20150379; Feb. 16, 2015; 1 page.*

* cited by examiner

*Primary Examiner* — Kent L Bell
(74) *Attorney, Agent, or Firm* — Barbara Campbell; Cochran Freund & Young LLC

(57) ABSTRACT

A new variety of *Zamioculcas* plant named 'Dowon' that is characterized by an erect vase-shaped habit, and stiffly-held compound, glossy leaves which emerge mid-green maturing to black, is described.

8 Drawing Sheets

Genus and species: *Zamioculcas zamiifolia.*
Variety denomination: 'Dowon'.

CROSS-REFERENCE TO RELATED APPLICATIONS

A Community Plant Variety Rights application was filed with the Community Plant Variety Office of Feb. 16, 2015, File Number 2015/0379; and Plant Breeders Rights were granted for this variety with the Department of Plant Variety Protection—Korea Forest Service on Dec. 26, 2013, Registration Number 4721. This variety has not been made publicly available or sold more than one year prior to the filing date of the present application.

BACKGROUND OF THE NEW PLANT

The present variety relates to a new and distinct variety of *Zamioculcas* commonly known as Aroid Palm or ZZ Plant. The new variety is known botanically as *Zamioculcas zamiifolia* and will be referred to hereinafter by the name 'Dowon'.

*Zamioculcas* is a succulent plant with dark green glossy compound leaves which stores water in its thick petioles. *Zamioculcas* is native to tropical and sub-tropical east and southeast Africa and only one species, *zamiifolia*, is known. *Zamioculcas* is grown and used as a tropical or indoor foliage plant.

*Zamioculcas* plants grow from an underground tuber which also comprises the stem. All of the growth above ground consists of erect or semi-erect large pinnately compound leaves borne on stiff petioles. Each leaflet within the compound leaf is attached to a central rachis. The attachment is typically sessile or minutely petiolulate.

The new *Zamioculcas* variety named 'Dowon' was discovered in 2006 as a naturally occurring branch mutation by the inventor at the inventor's nursery in Segok-dong, Seoul, South Korea. The inventor observed that a single unnamed plant of typically green-foliaged *Zamioculcas* had produced on one of its compound leaves a set of leaflets with uncharacteristically very dark green coloration, tending to darken further as the leaflets expanded. When fully expanded, the leaflets, rachis and petiole became entirely black or near-black. *Zamioculcas* may be propagated from individual leaflet cuttings. The inventor continued to observe the original plant for many months before carrying out the first asexual propagation in 2006 using black leaflets. The inventor was interested to know if the black leaflets would root and would produce new plants with the same characteristic of leaf blackening. The inventor observed that new foliage growth from the rooted black leaflets first emerged typically green in color but became black or nearly black as the compound leaf expanded and matured.

The inventor has repeated this process of reproduction from black leaves and has determined that the development of black plants as herein described is consistent. The inventor has determined that 'Dowon' reproduces true to type in successive generations of asexual reproduction via leaflet cuttings.

SUMMARY

The following traits have been repeatedly observed and represent the distinguishing characteristics of the new *Zamioculcas* variety named 'Dowon'. In combination these traits set 'Dowon' apart from its species and from all other varieties of *Zamioculcas* known to the inventor. 'Dowon' has not been tested under all possible conditions and phenotypic differences may be observed with variations in environmental, climatic and cultural conditions, however, without any variance in genotype:

1. Plants of 'Dowon' are erect and vase-shaped, consisting of stiffly held compound leaves.
2. The leaflets of the compound leaves of 'Dowon' are borne predominantly in opposite pairs. Some leaf pairs are sub-opposite or closely alternate.
3. The leaflets of 'Dowon' are very closely attached, either sessile or minutely petiolulate, to a central rachis.
4. The first emerging foliage growth of 'Dowon' is bright glossy mid-green in color.
5. As each new compound leaf ages over a period of 1 to 2 months, the color of the leaf darkens through dark olive green, then developing streaks or patches of very dark green tending to black, to eventually entirely black.
6. Mature compound leaves, including petioles, rachis and leaflets of 'Dowon' are entirely black.
7. The leaf surfaces of 'Dowon' are glossy.
8. The inflorescence of 'Dowon' emerges at or just above ground level and consists of a pale green spathe surrounding a cream-white spadix.

DESCRIPTION OF THE PHOTOGRAPHS

The accompanying color photographs illustrate the overall appearance of 'Dowon' showing the colors as true as it is reasonably possible to obtain in colored reproductions of this type. Colors in the photographs may differ from the color values cited in the detailed botanical description, which accurately describe the actual colors of the new variety 'Dowon'. Except for FIG. 9 which was taken in Miami, Fla., all photographs have been made from plants which have been grown by the inventor at the inventor's nursery in Seoul, South Korea. No growth regulators have been applied to any of the plants in the drawings.

DESCRIPTION OF THE NEW VARIETY

Figure 1:
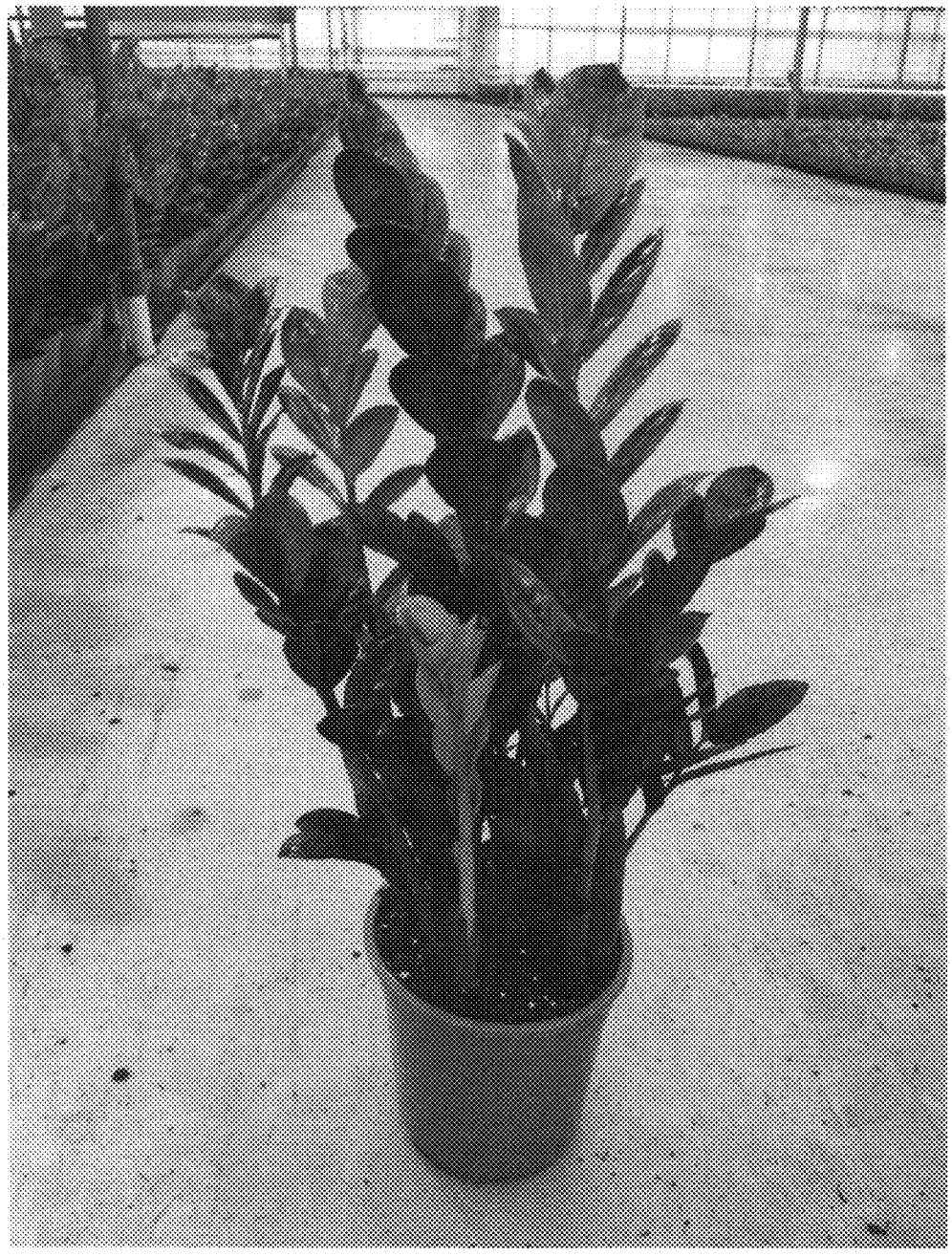
FIG. 1 shows a 9 months old plant of 'Dowon' in all stages of foliage color development.
Figure 2:
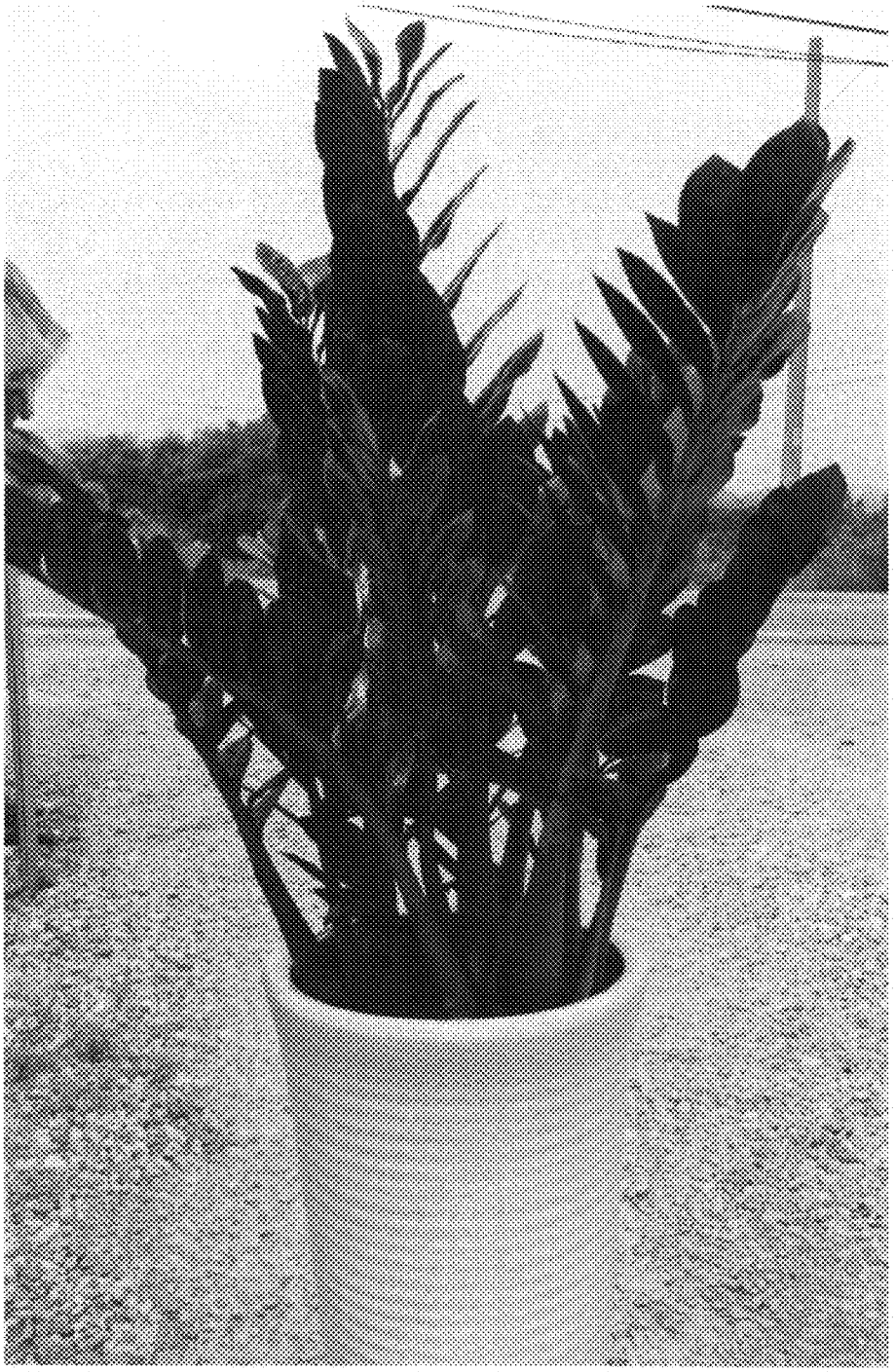
FIG. 2 shows a one year old plant of 'Dowon' which is fully mature and is not producing any new green foliage.
Figure 3:
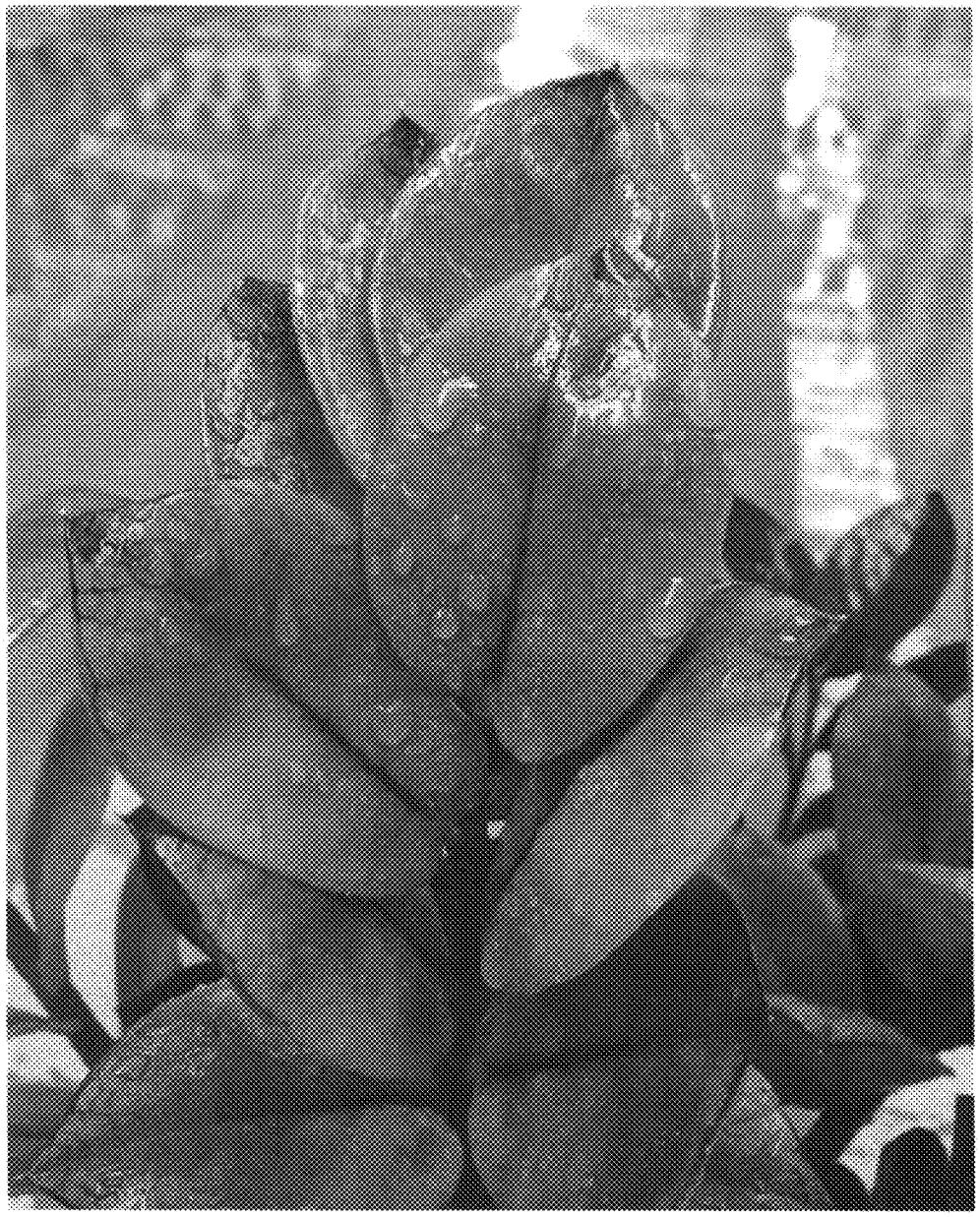
FIG. 3 depicts a close-up view of the leaflets of 'Dowon' as they begin to darken at around 6 months after emergence of the compound leaf. The vein midribs are prominent at this stage.
Figure 4:
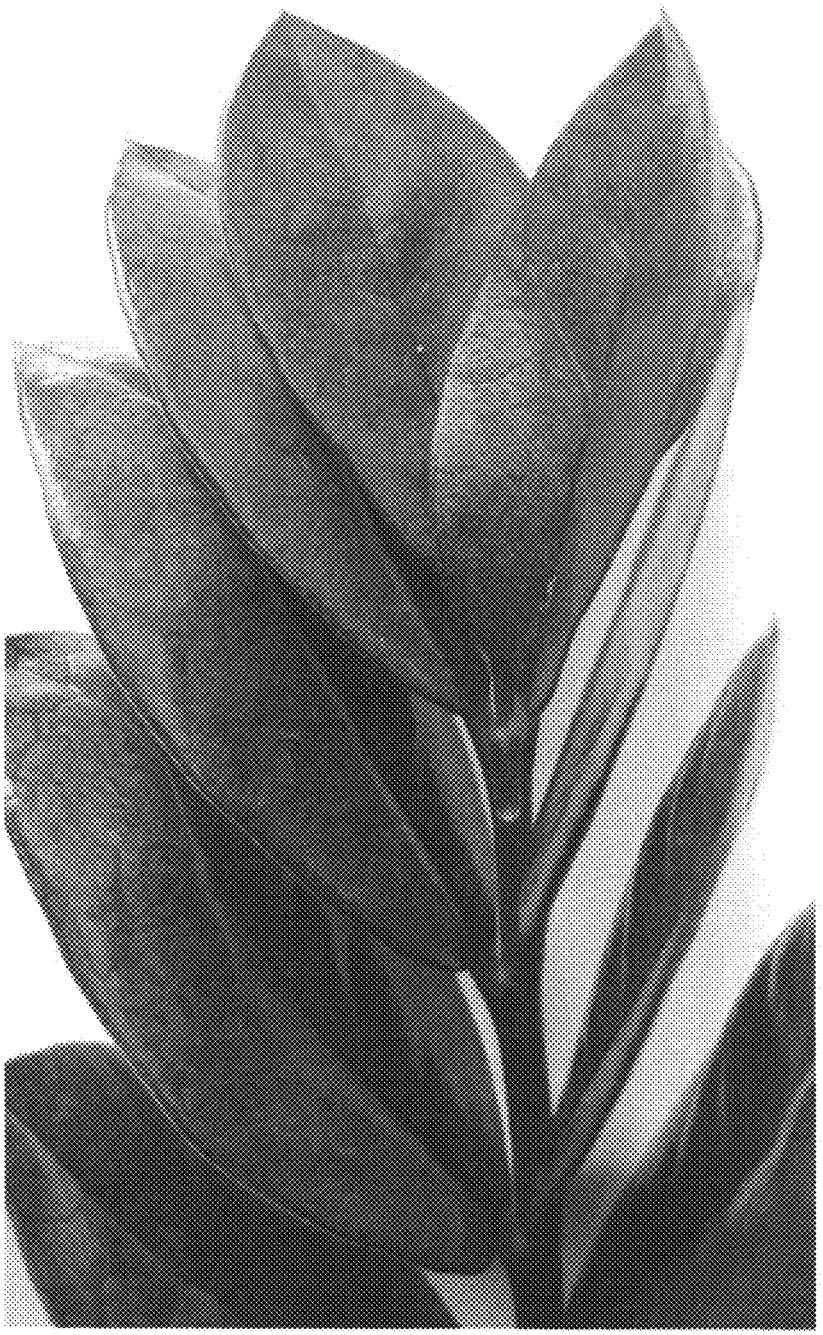
FIG. 4 depicts a compound leaf and leaflets of 'Dowon' which are in the mid-stage of turning from green to black, at around 6-9 months after emergence of the compound leaf.
Figure 5:
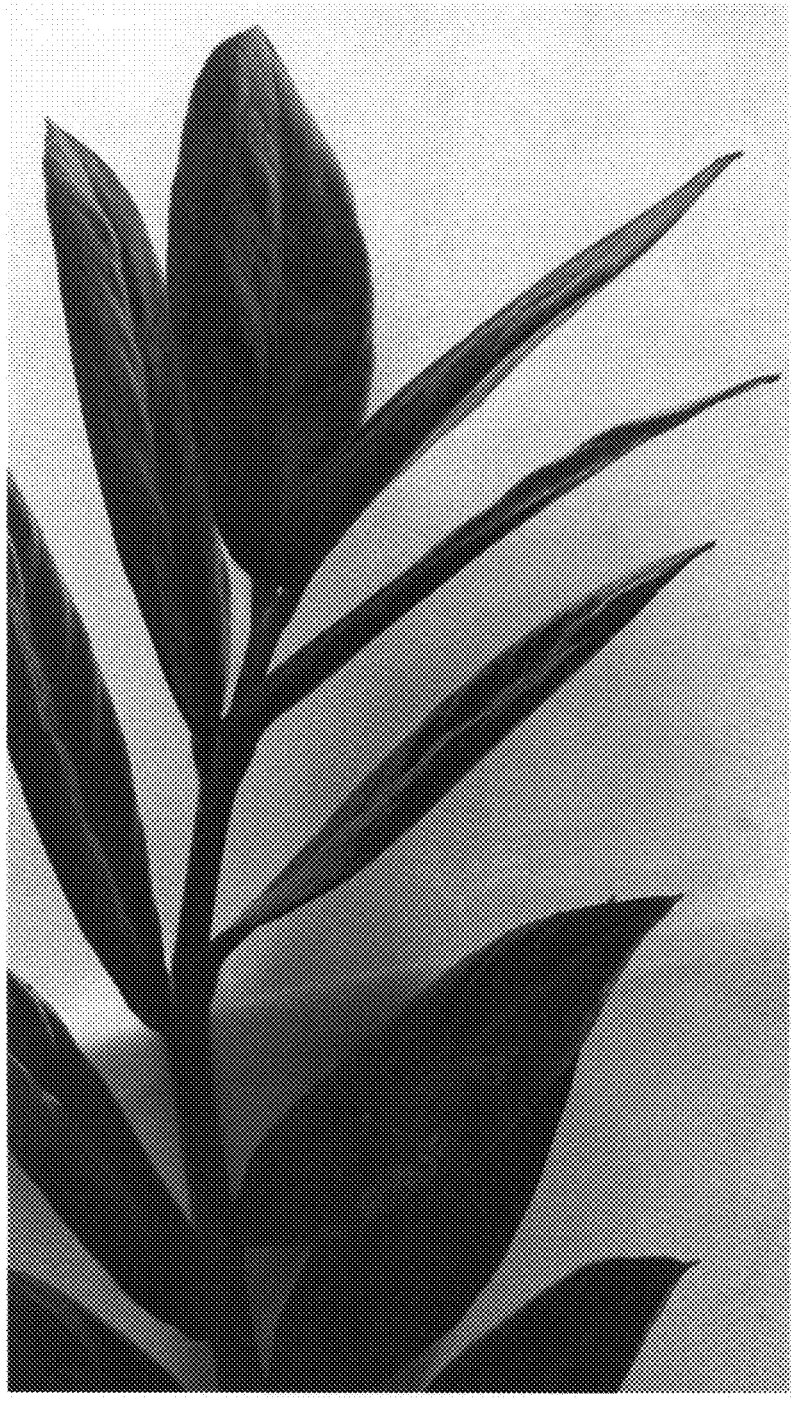
FIG. 5 depicts a compound leaf of 'Dowon' which has matured to entirely black in color. An individual compound leaf becomes entirely black around 12 months after its emergence.
Figure 6:
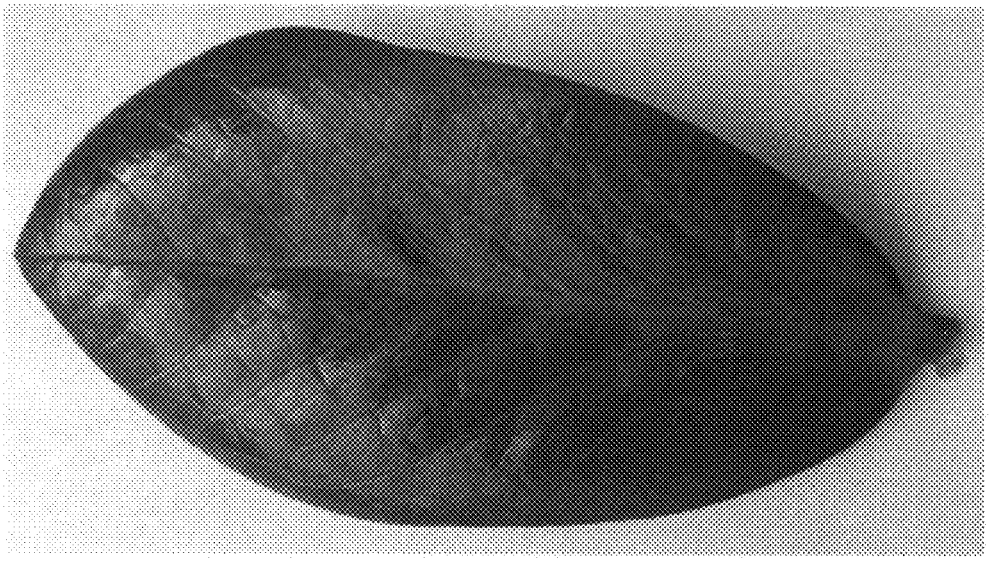
FIG. 6 depicts a leaflet of 'Dowon' in its semi-mature (olive green color) condition.
Figure 7:
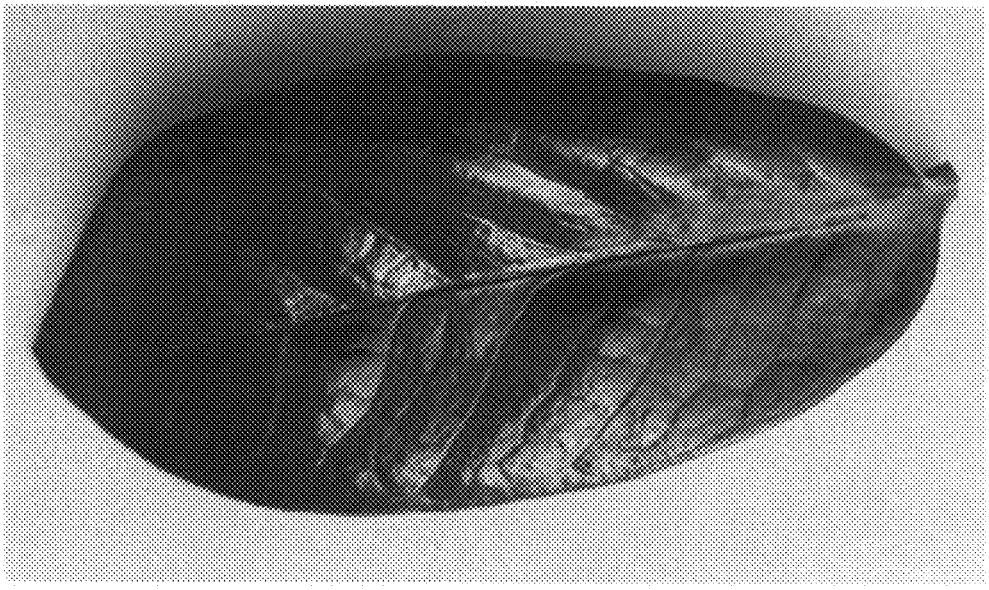
FIG. 7 depicts a leaflet of 'Dowon' in its mature (black color) condition.
Figure 8:
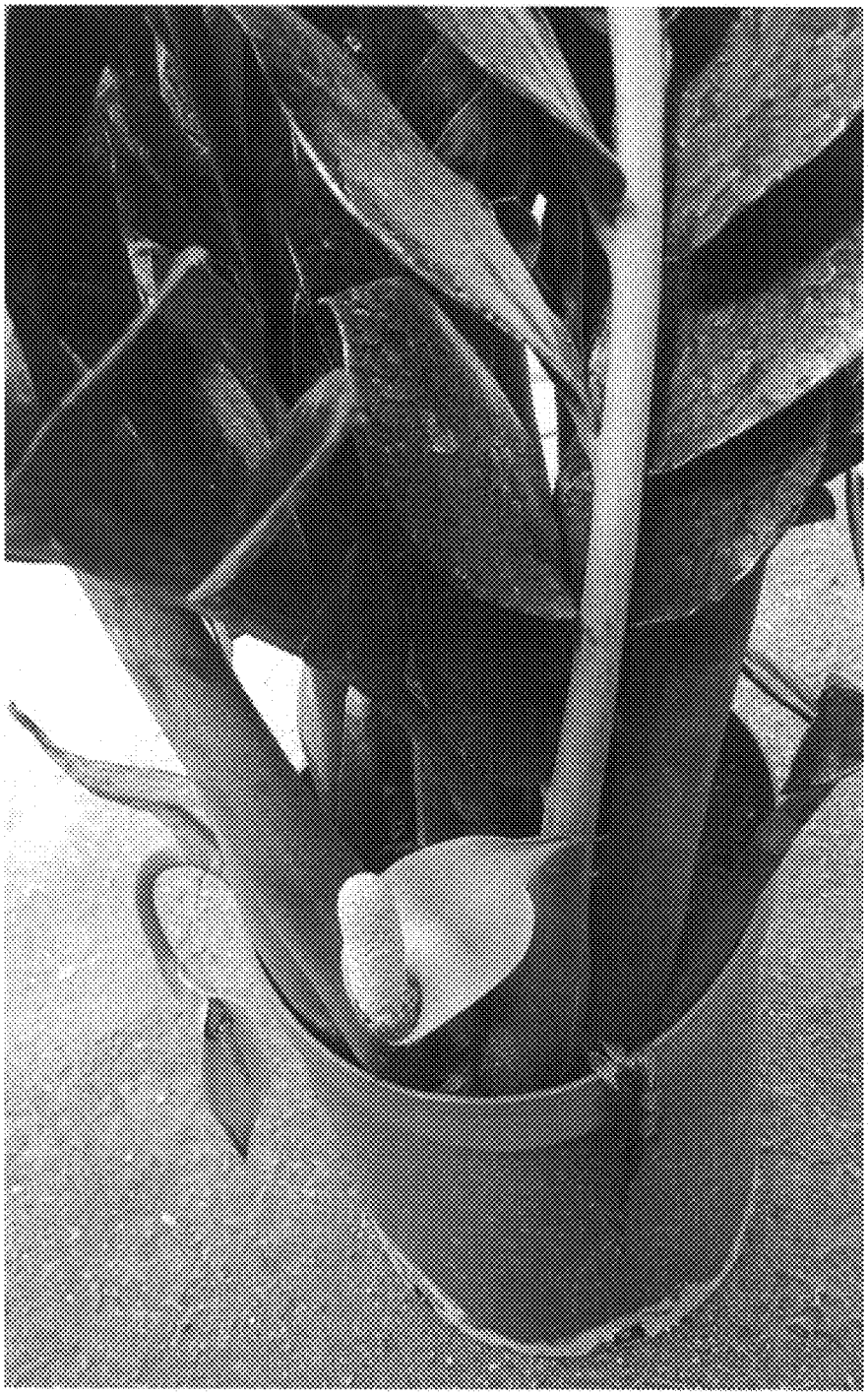
FIG. 8 depicts a fresh inflorescence (spathe and spadix) of 'Dowon' and an unfertilized aged inflorescence with strongly recurved peduncle, spathe and spadix. These inflorescences were observed on a mature plant of 'Dowon' which was at least 2 years old.
Figure 9:
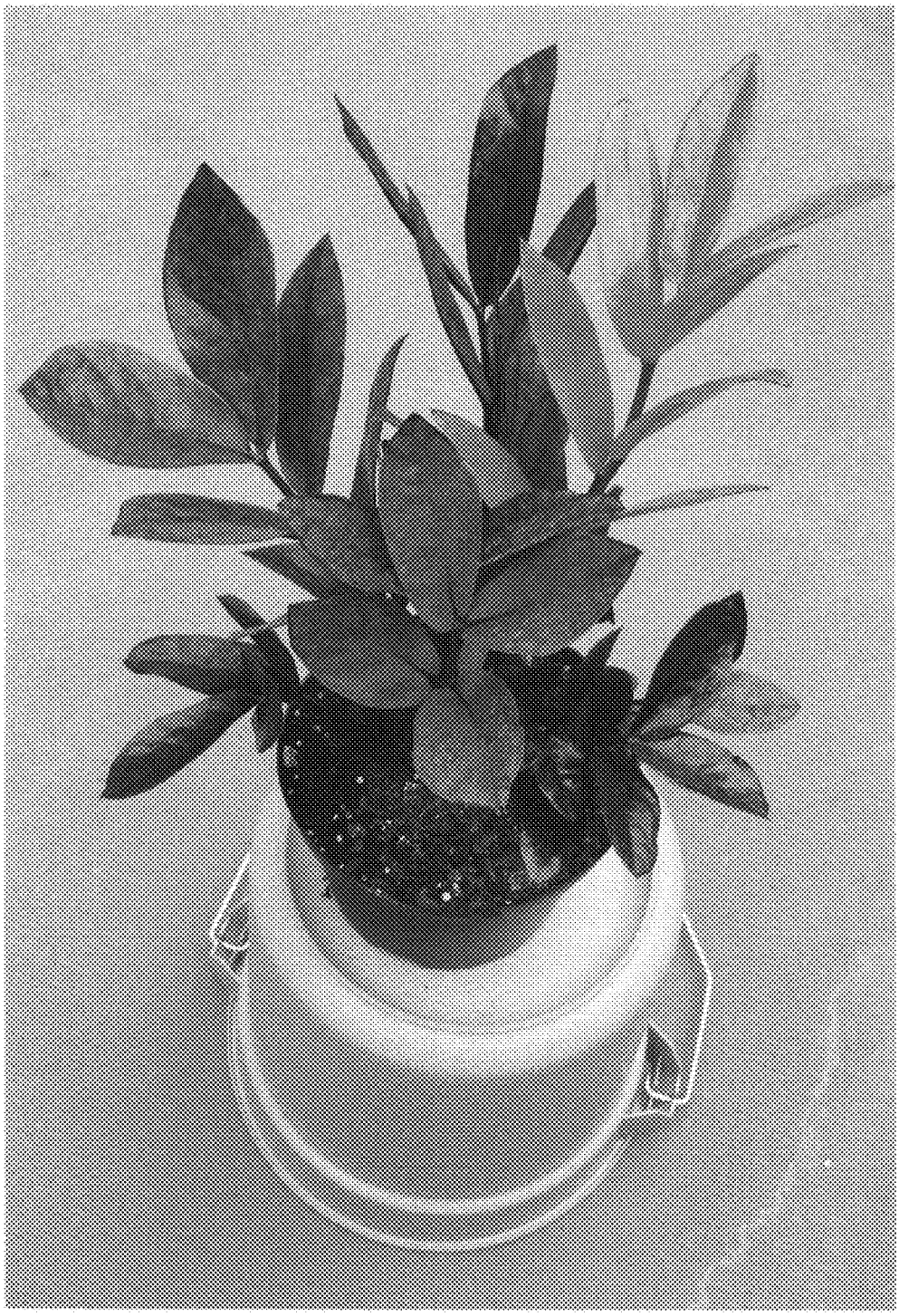
FIG. 9 depicts a six month old plant of 'Dowon' which has been grown out of doors in a 1-gallon container in Miami, Fla. and from which the detailed botanical description has been made.

The following is a detailed description of the new *Zamioculcas* plant named 'Dowon'. Data was collected in Santa Barbara, Calif. using six-month-old plants which were grown from a rooted leaflet from Miami, Fla. The description of the inflorescence of 'Dowon' was prepared from plants grown by the inventor in South Korea. The color determinations are in accordance with the 2007 edition of The Royal Horticultural Society Colour Chart, London, England, except where general color terms of ordinary dictionary significance are used. The growing requirements are similar to other *Zamioculcas*.

Botanical classification:

*Genus.*—*Zamioculcas.*

*Species.*—*zamiifolia.*

*Denomination.*—'Dowon'.

*Common name.*—Aroid Palm.

Parentage: Naturally occurring branch mutation from *Zamioculcas zamiifolia* (unnamed, unpatented).

Plant:

*Plant height.*—30.0 cm.

*Plant width.*—22.0 cm in width.

*Roots description.*—Fleshy; coarsely lateral branching; 1.0 mm to 3.0 mm in diameter; very fine root hairs; root color is 158A.

*Root development.*—At soil temperatures 20° C. to 25° C., root initials are evident within 3 days; roots will reach the edge of a 1-gallon container in 21 days.

*Time to develop roots.*—14 days at air and soil temperature of 25° C.

*Propagation type.*—Asexual reproduction is accomplished by leaflet cuttings.

*Plant vigor.*—Vigorous; prolific production of new leaves emerging from underground stem; 6 to 8 compound leaves per plant.

*Plant growth rate.*—A 1-gallon container plant may be produced in 12 to 16 weeks from a 4.0-cm cell transplant, or in 5 to 6 months from insertion of a leaflet cutting.

*Plant growth habit and shape.*—Upright and vase-shaped.

*Plant hardiness.*—None; 'Dowon' does not tolerate freezing conditions.

*Cultural requirements.*—'Dowon' thrives in high temperatures (above 70° F.), in full-sun or partial-shade.

*Use.*—Interior decorative landscaping; outdoor landscaping in regions with no frost.

Tuber (underground stem):

*Shape and dimensions.*—Short cylindrical; 5.0 cm in length, 2.0 cm to 3.0 cm in diameter.

*Surface texture.*—Rough with root initials and leaf initials.

*Color.*—Ranges between 158A and 165D.

Foliage (compound leaves):

*Quantity per plant.*—6 to 8 compound leaves arise from underground stem.

*Petiole dimensions and shape*.—Up to 10.0 cm in length; shape is cylindrical; diameter tapers from 10.0 mm at emergence from surface to 6.0 mm below lowest leaflet.

*Petiole surface and color*.—Smooth, glabrous, strong and stiff; color is 152D (new green growth) and 202A (mature, black growth).

*Rachis dimensions*.—Up to 15.0 cm in overall length with internode distance varying from 6.0 mm (between near-opposite leaflets) to 35.0 mm between leaflets furthest apart.

*Rachis surface and color*.—Smooth, glabrous, strong and stiff; color is 152D (new green growth) and 202A (mature, black growth).

Foliage (leaflets):

*Quantity per compound leaf*.—Up to 30 leaflets on the oldest compound leaves on a mature, 2 year old plant.

*Attachment*.—Sessile or minutely petiolulate.

*Arrangement*.—Predominantly alternate, internode distance ranges between 5 mm and 35 mm. Leaflets occasionally opposite.

*Dimensions* (*largest*).—9.0 cm in length and 4.7 cm in width.

*Aspect*.—Erect, held between 30° and 45° away from the rachis.

*Shape*.—Obovate-elliptic.

*Apex*.—Acuminate, point extends 1.5 mm.

*Base*.—Cuneate-rounded, occasionally oblique.

*Margin*.—Entire, smooth.

*Surface texture* (*both surfaces*).—Glabrous, glossy.

*Color* (*both surfaces*).—New green growth: 144A. Semi-mature growth: Mottled 139A against 146A. Mature black growth: 203B.

*Venation*.—Pinnate, not prominent; appears as shallow depressions on adaxial surfaces and shallow ridges on abaxial surfaces.

*Vein color* (*new green growth, both surfaces*).—144A or very slightly lighter.

*Vein color* (*semi-mature growth, adaxial surface*).—Midrib is 187A; elsewhere is 146A or slightly lighter.

*Vein color* (*semi-mature growth, abaxial surface*).—Ranges between 139A and 146A.

*Vein color* (*mature growth, both surfaces*).—203B. Petiolules (where present): Dimensions: Length is 1.0 mm to 3.0 mm and diameter is 1.0 mm to 3.0 mm. Shape: Sulcate. Surface texture: Smooth. Color: 144A (new green growth); 139A (semi-mature growth); and 203B (mature black growth).

Inflorescence:

*General*.—Spadix flowers not closely observed; pollination has not been observed.

*Spathe*.—Appearance: Short cylindrical tube with longer ovate blades, 5.0 cm to 6.0 cm in length and 4.0 cm to 5.0 cm in width. Length: 1.5 cm. Diameter: 1.5 cm. Apex: Acuminate, point extends up to 1.0 cm. Base: Sheathing. Margin: Entire, smooth. Spathe color (both surfaces): Ranges between NN155C and 145C. With age: Contracts with age.

*Spadix*.—Shape: Tapering cylindrical. Length: 6.0 cm. Diameter: 1.5 cm at widest, narrowed to 1.0 cm at the base. Color: NN155D. With age: Contracts with age.

*Peduncle*.—Appearance: Short and erect. Length: Approximately 2.0 cm. Diameter: 0.5 cm. Color: N189B. Texture: Glabrous. With age: Peduncle extends and becomes strongly recurved, approximately 8.0 cm in length, 0.5 cm in diameter, and color fades to N187B.

Resistance or susceptibility to pests and diseases: 'Dowon' has been observed to be less attractive to common pests which affect indoor plants including mites (*Tetranychidae*), aphids (*Aphididae*) and mealybugs (*Pseudococcidae*).

COMPARISON TO PARENTAL LINE

'Dowon' may be compared with its sport parent, an unnamed plant of *Zamioculcas zamiifolia*. Whereas the compound leaves (including leaflets, rachis and petiole) of the unnamed *Zamioculcas zamiifolia* are green in color, a mature plant of 'Dowon' is uniformly black or near-black. In addition, the inventor has observed that 'Dowon' is less attractive to common pests which affect indoor plants including mites, aphids and mealybugs.

'Dowon' may also be compared with the unnamed parent plant of *Zamioculcas zamiifolia* by the additional growing time required for a same-sized plant to become saleable with black foliage. Altogether, the inventor has observed that a mature (60.0 cm in height) fully-black plant of 'Dowon' may take 9 to 12 months to produce compared with 3 to 4 months for production of green *Zamioculcas zamiifolia*.

The closest known variety of *Zamioculcas*' which exhibits black or near-black foliage is *Zamioculcas* plant named 'Dark Zamicro' (U.S. Plant Pat. No. 28,847). Whereas 'Dowon' is a vigorous variety, 'Dark Zamicro' grows with low to moderate vigor and bears smaller leaflets.

I claim:

1. A new and distinct variety of *Zamioculcas* plant named 'Dowon' as illustrated and described herein.

* * * * *